(12) United States Patent
Tornier

(10) Patent No.: US 6,969,406 B2
(45) Date of Patent: Nov. 29, 2005

(54) PROSTHETIC ELEMENT COMPRISING TWO COMPONENTS AND PROCESS FOR ASSEMBLING SUCH A PROSTHETIC ELEMENT

(75) Inventor: Alain Tornier, Saint Ismier (FR)

(73) Assignee: Tornier SA, Saint Ismier (FR)

( * ) Notice: Subject to any disclaimer, the term of this patent is extended or adjusted under 35 U.S.C. 154(b) by 0 days.

(21) Appl. No.: 10/357,384

(22) Filed: Feb. 4, 2003

(65) Prior Publication Data

US 2003/0149485 A1 Aug. 7, 2003

(30) Foreign Application Priority Data

Feb. 4, 2002 (FR) .................................. 02 01284

(51) Int. Cl.[7] .............................................. A61F 2/40
(52) U.S. Cl. ............................. 623/19.13; 623/22.43; 623/23.11; 623/23.15; 606/62
(58) Field of Search .................... 623/19.11, 19.12, 623/19.13, 19.14, 20.28, 20.29, 20.33, 20.34, 623/20.36, 22.43, 23.18, 23.11, 23.14, 23.17, 623/22.12, 23.15; 606/60, 63, 67

(56) References Cited

U.S. PATENT DOCUMENTS

| | | | |
|---|---|---|---|
| 3,530,854 A | * | 9/1970 | Kearney ...................... 606/67 |
| 5,334,184 A | * | 8/1994 | Bimman ...................... 606/63 |
| 5,782,920 A | * | 7/1998 | Colleran ................... 623/20.34 |
| 6,102,951 A | | 8/2000 | Sutter et al. |
| 6,136,032 A | | 10/2000 | Perice et al. |

FOREIGN PATENT DOCUMENTS

| | | |
|---|---|---|
| EP | 0552950 | 7/1993 |
| EP | 0634154 | 1/1995 |
| EP | 0815808 | 1/1998 |
| EP | 0884032 | 12/1998 |
| FR | 2605514 | 4/1988 |
| FR | 2689756 | 10/1993 |
| FR | 2704747 | 11/1994 |
| FR | 2737107 | 1/1997 |
| GB | 2375052 | 11/2002 |
| WO | 0147441 A1 | 7/2001 |

* cited by examiner

Primary Examiner—Bruce E. Snow
(74) Attorney, Agent, or Firm—Dowell & Dowell, P.C.

(57) ABSTRACT

A prosthetic element comprising two principal components which are assembled together and immobilized with respect to each other by a screw which may be selectively threaded into at least one tapping in at least one of the principal components. The screw comprises at least one radial element adapted to abut against a stop surface within the first component, and a non-threaded end forming a guide which is adapted to slide in a bore in the second component.

20 Claims, 7 Drawing Sheets

PROSTHETIC ELEMENT COMPRISING TWO COMPONENTS AND PROCESS FOR ASSEMBLING SUCH A PROSTHETIC ELEMENT

BACKGROUND OF THE INVENTION

1. Field of the Invention

The present invention relates to a prosthetic element comprising two principal components, to the use of such an element, and to processes for assembly of such an element.

2. Description of the Related Art

A prosthetic element most often comprises a part intended to constitute an articular surface and a part for anchorage in the patient's bone. Taking into account their respective mechanical functions, these parts are sometimes composed of distinct components, such components each being optimalized as far as the choice of their constituent materials and their mode of manufacture are concerned. These components should then be able to be assembled precisely and easily. For example, an anchoring component may be fixed in the bone and a component forming an articular surface added thereon.

In certain prior art devices, such as disclosed in FR-A-2 605 514 for example, it is known to use a screw for locking one part of a prosthesis on another part provided with a corresponding tapping. It is also known from FR-A-2 689 756 to use a screw for locking a shank fast with an articular head inside a bore made in a prosthesis anchoring part. It is also possible, as in FR-A-2 737 107, to provide using a screw captive in a housing made on one of the parts and intended to cooperate with a tapping made in the other part.

The known devices require precise positioning and alignment of the components constituting a prosthetic element, which is not always possible as the operative field is difficult to access and as it is delicate to visualize due to the traumatic depression of the glenoid cavity. In addition, the screws used in the known system may be displaced or poorly aligned with respect to the parts with which they are to cooperate, hence a risk of distorting their threads or the tapping with which they are to cooperate.

It is a more particular object of the present invention to overcome these drawbacks by proposing a prosthetic element that may be assembled in particularly easy and precise manner, while remaining very practical to use.

SUMMARY OF THE INVENTION

To that end, the present invention relates to a prosthetic element which comprises two principal components intended to be assembled together and immobilized with respect to each other by means of a screw, this prosthetic element being characterized in that the screw is adapted to be screwed by means of at least one thread in two tappings which are respectively fast or intended to be rendered fast with one and the other principal components and in that the screw comprises at least one radial element in relief adapted to come into abutment against a stop surface fast with a first component, and a non-threaded end forming guide finger and adapted to slide in a housing made in the second component.

Thanks to the invention, the locking screw may be immobilized with respect to one of the principal components, this guaranteeing its positioning and orientation with respect thereto. Then, when its guide finger is inserted in the housing of the second component which has a transverse section corresponding to that of the finger, the components are guided with respect to one another in a movement of mutual approach. The radial element in relief provided on the screw allows it to exert on the stop surface an effort directed towards the second component, in order to firmly apply these components against one another and thus to contribute to their relative immobilization, after screwing of the screw in the second tapping.

According to advantageous but non-obligatory aspects of the invention, this prosthetic element incorporates one or more of the following characteristics:

- the element of the screw in relief is formed by a radial flange made on the screw between the two threads thereof.
- the stop surface is annular and surrounds this screw. In that case, this stop surface may be provided to be formed by the face of a ring surrounding the screw, this ring being rigidly connected to a bush screwed in the first component. This ring and this bush allow an efficient transmission of effort between the screw and the first component.
- the first and second components are respectively provided with truncated bearing surfaces, the screw being adapted to apply, by its screwing, these surfaces against each other. This aspect of the invention takes advantage of the fact that the screw of the invention guarantees satisfactory positioning and movement of approach of the truncated bearing surfaces provided respectively on the first and second components, this limiting the risks of misalignment of these surfaces. These bearing surfaces are advantageously respectively centred on the central axis of the screw, when the latter is screwed in the first component, and on the central axis of the housing for slide of the centering finger.
- the tapping which is fast or intended to be rendered fast with the second component is formed in the housing for slide of the centering finger, towards an inlet zone of the screw.
- the first component forms a convex articular surface and defines a volume in which the screw may be mounted and the second component engaged, at least partially. The first component may for example be in the form of a portion of sphere.
- the housing for slide of the guide finger is made in a shank for anchoring the second component in a bone.

According to a first advantageous form of embodiment of the invention, the screw is provided with two threads adapted to cooperate successively with two tappings respectively fast with one and the other principal components.

According to a second advantageous form of embodiment of the invention, the screw is provided with a single thread adapted to cooperate successively with two tappings which are respectively fast or intended to be rendered fast with one and the other of the principal components.

A prosthetic element as described hereinabove can be used in particular in the production of the glenoid part of a total shoulder prosthesis.

The invention also relates to a first process for assembling a prosthetic element as described hereinabove and, more precisely, to a process which comprises steps consisting in:

- immobilizing the screw with respect to a first principal component of the prosthetic element by screwing this screw in a first tapping fast or intended to be rendered fast with the first principal component, a surface forming stop, at a distance from the screw with respect to the first component, being arranged around this screw after or before this immobilization;

covering with a housing made on a second component, a free end of the screw projecting with respect to the first component;

pushing the first and second components towards each other, causing the end of the screw to slide in the afore-mentioned housing;

unscrewing the screw with respect to the first tapping, and screwing the screw in a second tapping made in the second component, exerting on the afore-mentioned stop surface an effort of approach of the first and second components.

According to a second process of assembly in accordance with the invention, the screw is immobilized and its free end is covered as indicated hereinabove, following which:

one of the principal components is impacted in the direction of the other so as to bring them closer, causing the free end of the screw to slide in the housing, until the components are brought into contact with each other;

the screw is unscrewed with respect to the first tapping, and the screw is screwed in a second tapping made in the second component until an effort of relative immobilization of the components is obtained in their position in contact, this effort being exerted on the afore-mentioned stop surface.

Thanks to the processes of the invention, the screw is permanently correctly positioned with respect to the components constituting the prosthetic element, this ensuring for the surgeon precision of assembly.

BRIEF DESCRIPTION OF THE DRAWINGS

The invention will be more readily understood on reading the following description of two forms of embodiment of a prosthetic element and of its process of assembly in accordance with its principle, given solely by way of example and with reference to the accompanying drawings, in which.

DESCRIPTION OF PREFERRED EMBODIMENTS

Figure 1:
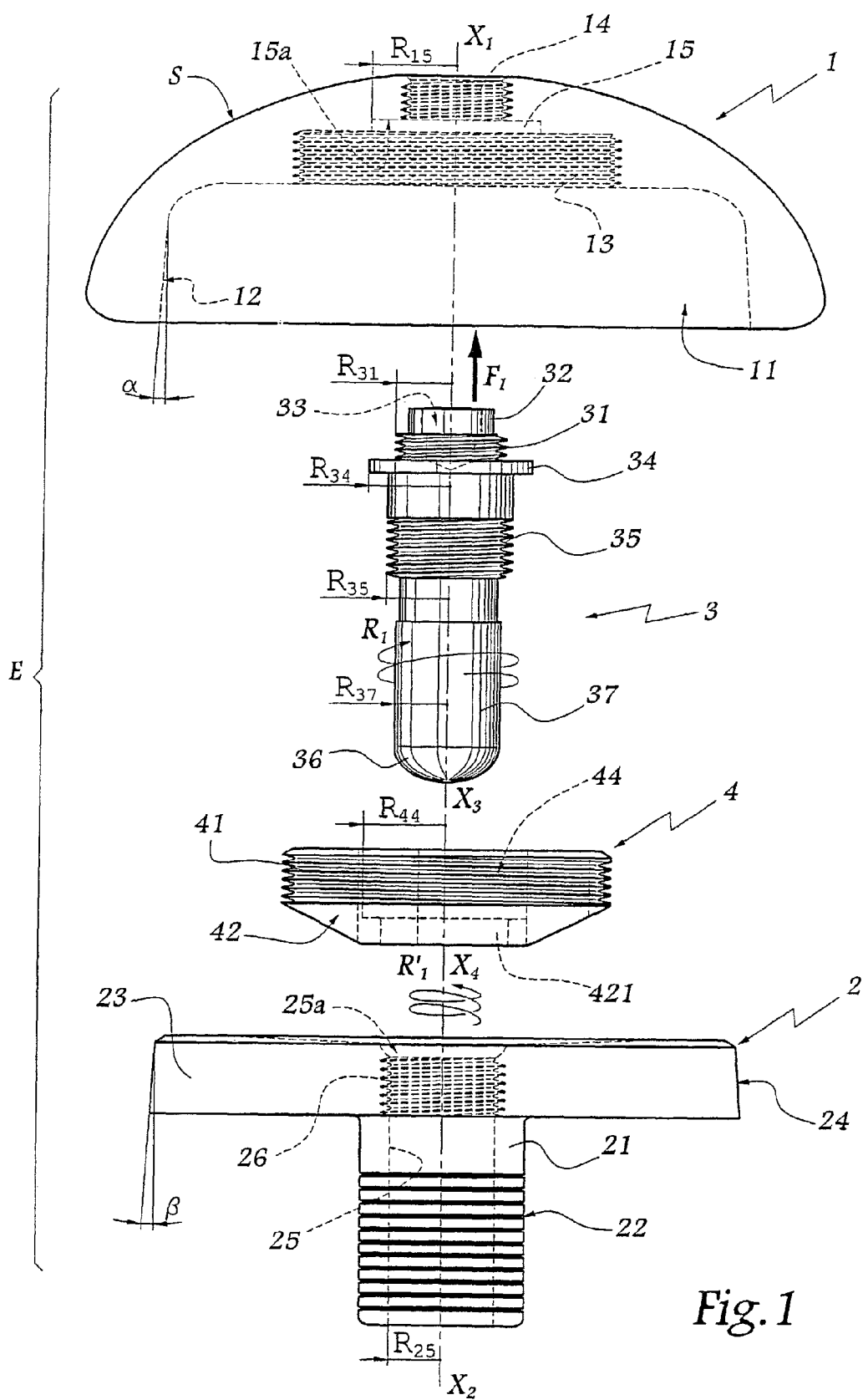
FIG. 1 is an exploded side view of a prosthetic element in accordance with a first form of embodiment of the invention.

Referring now to the drawings, the prosthetic element E shown in the Figures is intended to be mounted on a shoulder in order to constitute an articular surface S intended to cooperate with a cupule (not shown) belonging to a complementary prosthetic element anchored in the patient's humerus.

The surface S is approximately in the form of a portion of sphere and constitutes the outer surface of a first principal component 1 made of a material compatible with the movements of articulation on the cupule associated therewith.

$X_1$ denotes a central axis of the component 1 which constitutes a diameter of the surface S. The component 1 is provided with a central recess 11 centered on axis $X_1$ and of which 12 denotes the peripheral surface, this surface being of truncated shape.

A tapping 13 is provided at the bottom of the recess 11, centered on axis $X_1$.

A second tapping 14 is centered on axis $X_1$ and opens to the outside, at the surface S.

A circular bore 15 is made between the tappings 13 and 14, the radius $R_{15}$ of this bore being included between the radii of the tappings 13 and 14.

A second principal component 2 is provided to be anchored in the glenoid cavity of the shoulder and, to that end, comprises a shank 21 provided with grooves 22. $X_2$ denotes the axis of the shank 21 which is substantially cylindrical and of circular cross-section.

The component 2 also comprises a plate 23 which is solid and in one piece with the shank 21, this plate being provided with a truncated outer surface 24 centered on axis $X_2$.

The maximum radii of the surfaces 12 and 24 are substantially identical and their respective taper angles $\alpha$ and $\beta$ are identical, this making it possible to provide a surface bearing of these surfaces against each other.

The shank 21 is provided with a central bore 25, of cylindrical shape and which extends in the plate 23 via a tapping 26.

The element E also comprises a screw 3 of which $X_3$ denotes the longitudinal axis. This screw is provided with a first thread 31 intended to cooperate with the tapping 14 in order to immobilize the screw 3 on the component 1, axes $X_1$ and $X_3$ in that case merging.

32 denotes the end of the screw 3 towards the thread 31. This end is provided with a polygonal hollow housing 33 for receiving a wrench (not shown) allowing the screw 3 to be rotated about axis $X_3$.

The screw 3 is also provided with an outer radial flange 34 of which $R_{34}$ denotes the radius.

A second thread 35 is also provided on the screw 3, opposite thread 31 with respect to the flange 34. In other words, the flange 34 is disposed axially, along the screw 3, between the threads 31 and 35.

$R_{31}$ and $R_{35}$ respectively denote the radii of the threads 31 and 35. Radius $R_{34}$ is greater than radii $R_{31}$ and $R_{35}$, with the result that the flange 34 constitutes a radial element of the screw 3 in relief, particularly with respect to the threads 31 and 35.

The screw 3 comprises, towards its rounded end 36 opposite end 32, a cylindrical part 37 of circular cross-section of which $R_{37}$ denotes the radius.

Parts 36 and 37 of the screw 3 form a guiding and centering finger intended to slide in the bore 25 which is of circular cross-section and of which $R_{25}$ denotes the radius, this radius itself being slightly greater than radius $R_{37}$. The respective transverse sections of the housing 25 and of the part 37 correspond to each other, this making it possible to guide part 37, and consequently the centering finger, in translation when it slides in the housing or bore 25.

The tapping 26 and the thread 35 are provided to cooperate so as to allow the screw 3 to be screwed in the component 2 after introduction of the centering finger in the bore 25.

The tapping 26 is formed in the plate 23, i.e. on the side of introduction of the screw 3 in the housing 25. The inlet zone 25a of the housing 25 is of rounded and concave shape, which makes it possible to pre-center the end 36 when it is introduced in the housing 25.

In a variant embodiment, the zone 25a may be replaced by a truncated chamfer.

A threaded bush 4 is also provided. $X_4$ denotes its central axis and 41 its outer thread which is provided to cooperate with the tapping 13, in order to immobilize the bush 4 on the component 1, axes $X_1$ and $X_4$ in that case merging.

This bush comprises a ring 42 of which 421 denotes the inner radial surface and 422 the lateral surface facing the flange 34 when the pieces 3 and 4 are in the configuration of FIG. 1. The ring 42 is in one piece with the rest of the bush 4 and connected thereto by tabs 43 which may take any shape adapted to their function.

The bush 4 is provided with a central bore 44 of which $R_{44}$ denotes the radius, this radius being greater than radius $R_{34}$.

The prosthetic element E is assembled in the following manner:

The screw 3 is firstly introduced in the recess 11, in the direction of arrow $F_1$, until its thread 31 is taken in the tapping 14. It is then possible to the screw 3, causing it to undergo a movement of rotation represented by arrow $R_1$, by means of a wrench (not shown) introduced in the housing 33, from outside the component 1.

This operation makes it possible to immobilize the screw 3 on the component 1 by aligning axes $X_1$ and $X_3$.

The flange 34 is then received in the bore 15 and bears against the bottom 15a thereof. To that end, the radius $R_{15}$ is slightly greater than radius $R_{34}$.

It is then possible to screw the bush 4 in the tapping 13, as represented by arrow $R'_1$, the ring 42 in that case being disposed around the screw 3.

Figure 2:
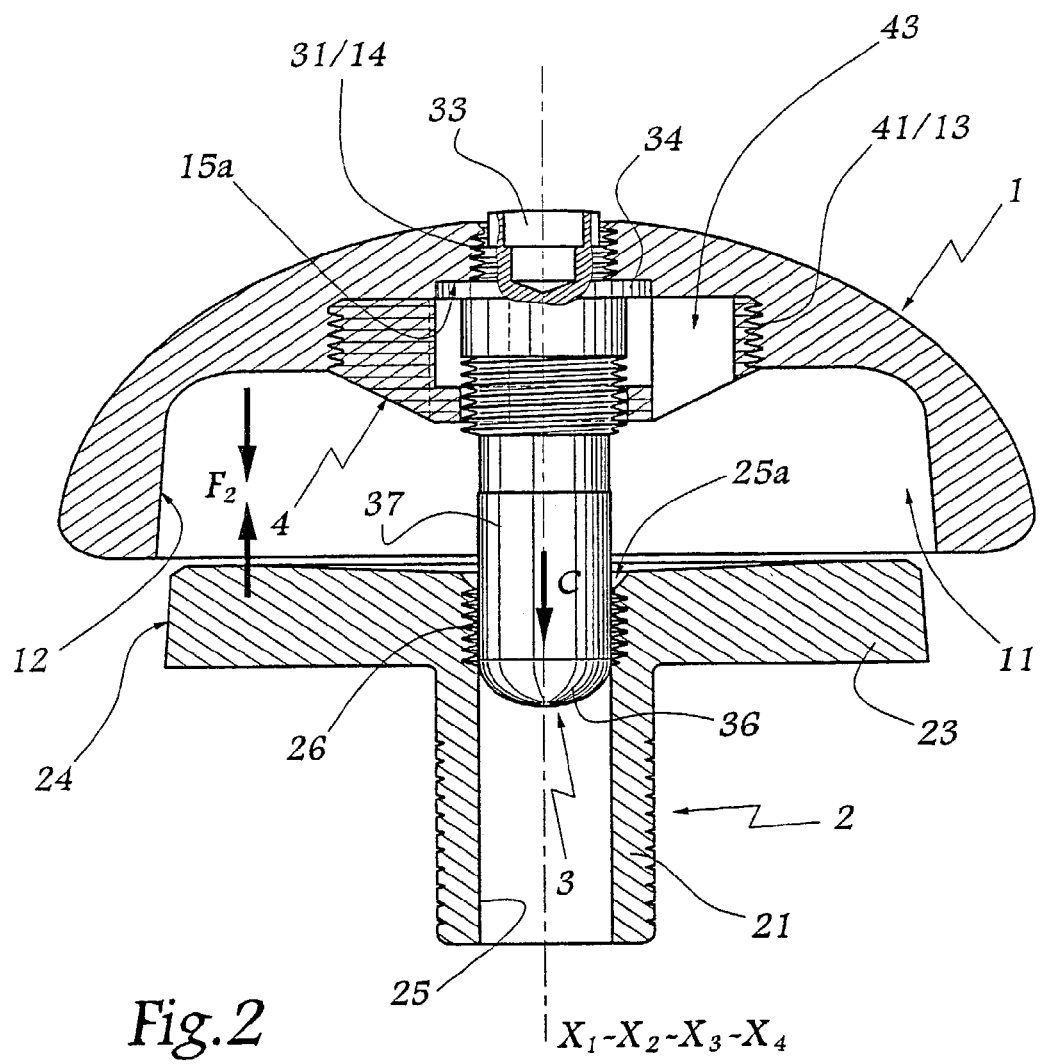
FIG. 2 is an axial section of the prosthetic element of FIG. 1, during a first step of its assembly.

The components 1 and 2 may then be brought closer to each other as represented by arrows $F_2$ in FIG. 2, which means causing the guiding and centering finger 36–37 to penetrate and slide in the bore 25, as represented by the arrow of slide C. This induces an alignment of axis $X_2$ on axes $X_1$ and $X_3$.

Figure 3:
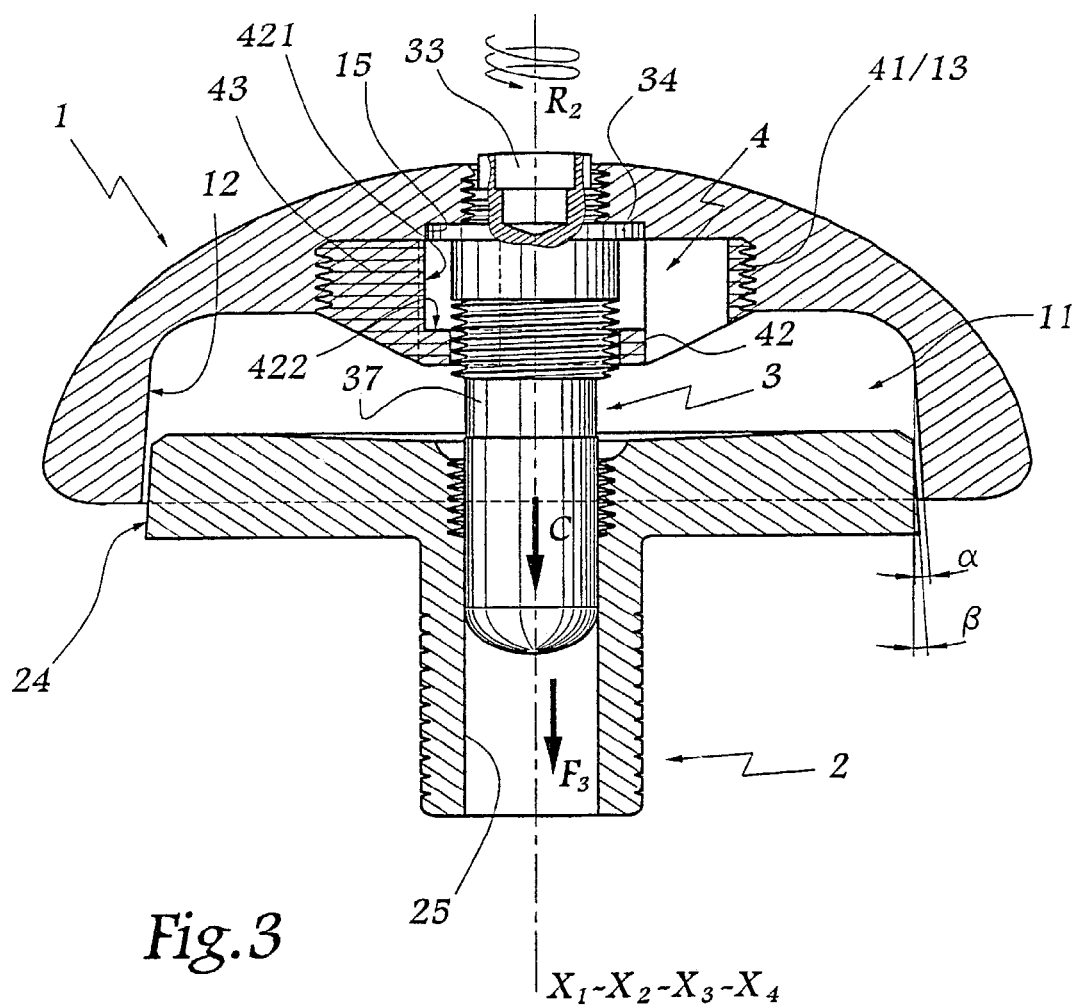
FIG. 3 is a section similar to FIG. 2, during a second step of assembly.

Components 1 and 2 may then be respectively advanced in the directions of arrows $F_2$ until surfaces 12 and 24 are brought into contact, as shown in FIG. 3.

Figure 4:
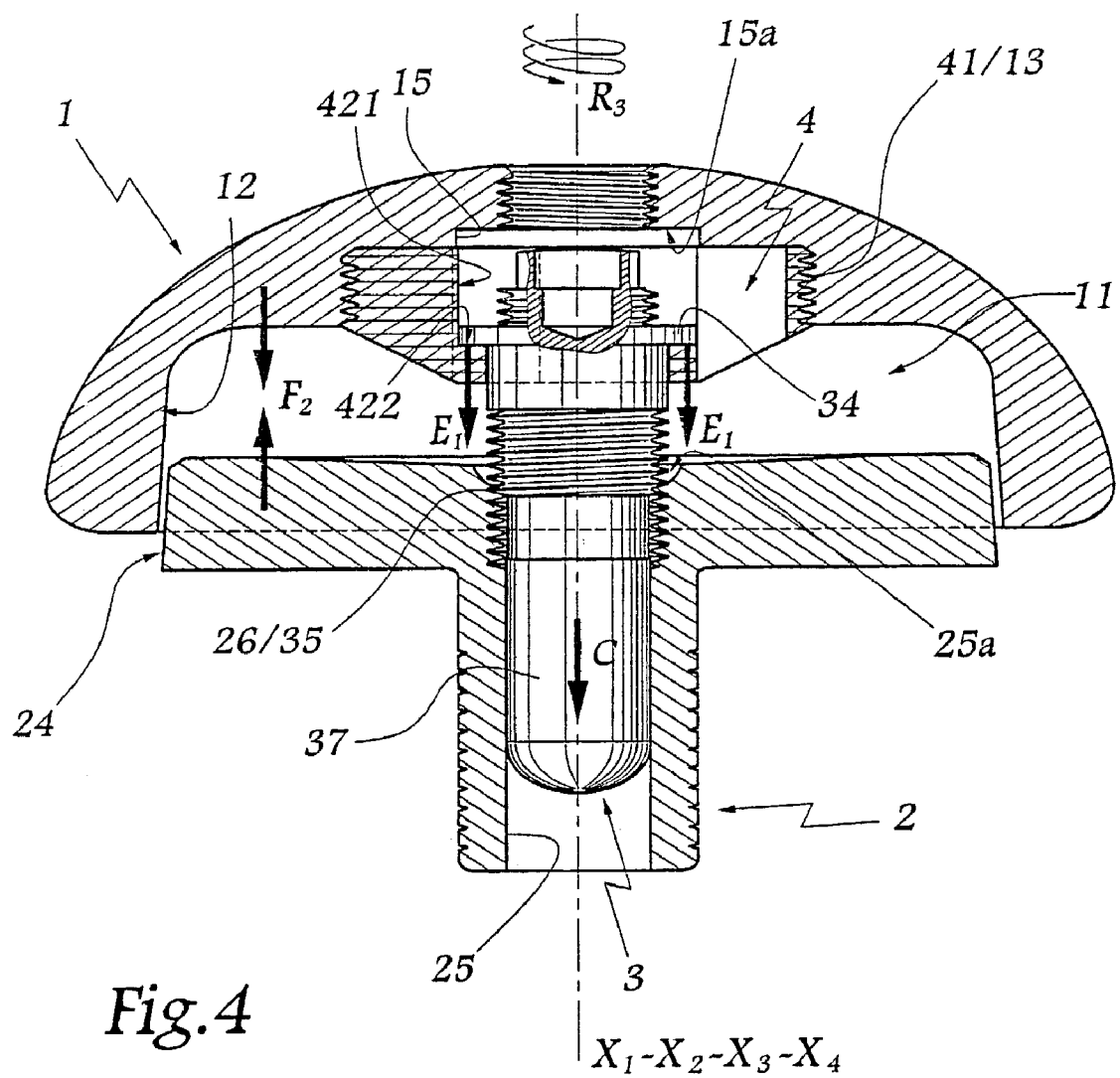
FIG. 4 is a section similar to FIG. 2, during a third step of assembly.

It is then possible to unscrew the screw 3 with respect to the tapping 14, as represented by arrow $R_2$ in FIG. 3, then to push the screw 3 in the direction of the component 2 as represented by arrow $F_3$, which has the effect of bringing the thread 35 into contact with the tapping 26, the flange 34 in that case being in abutment against the surface 422 of the ring 42, as shown in FIG. 4.

Figure 5:
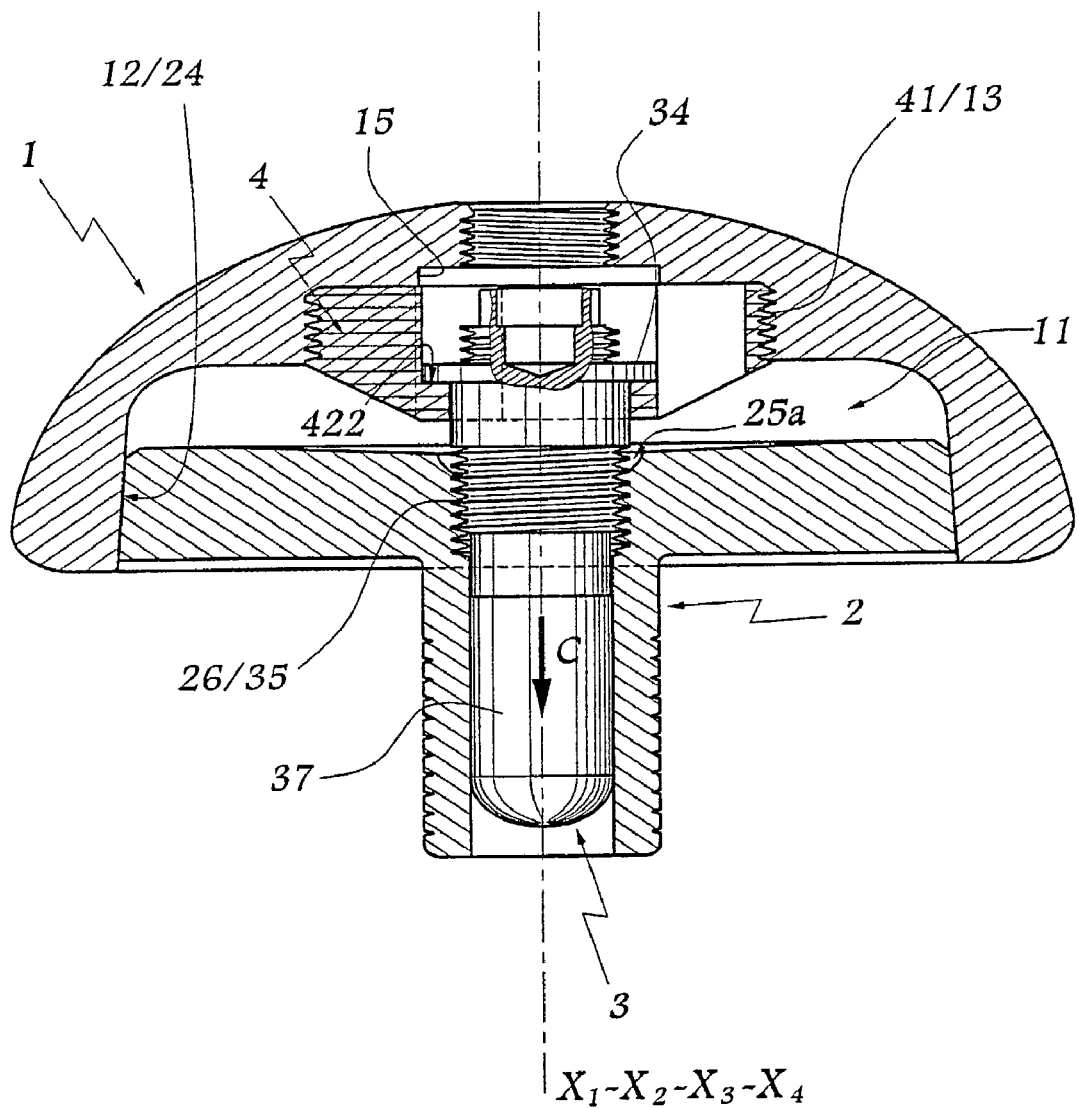
FIG. 5 is a section similar to FIG. 2, when assembly is terminated.

It is then possible to screw the screw 3 in the component 2 thanks to the thread 35 and to the tapping 26, as represented by arrow $R_3$ in FIG. 4, which has the effect of further approaching components 1 and 2 towards each other, as represented by arrows $F_2$. This makes it possible to pass from the configuration of FIG. 4 to that of FIG. 5, where the surfaces 12 and 24 are in firm abutment against each other, this guaranteeing the relative immobilization of components 1 and 2.

The threads 35 and 41 are of opposite directions, which avoids an untimely unscrewing of the bush 4 during screwing of the screw 3 in the tapping 26.

During screwing of the screw 3 on the component 2, the flange 34 exerts on the surface 422 of the ring 42 an effort $E_1$ parallel to axes $X_1$, $X_2$ and $X_3$ and directed towards the component 2, this effort being transmitted by the bush 4 to the component 1 which thus advances in the direction of the plate 23.

In a variant embodiment, in the position of contact between the thread 35 and the tapping 26, the flange 34 may be in the vicinity of the surface 422. In that case, the beginning of screwing of screw 3 on the component 2 causes the flange 34 and the ring 42 to approach each other, before the effort $E_1$ is applied.

In the course of the phases of assembly of the element E shown respectively in FIGS. 2 to 5, and as represented by arrow C, the guide finger constituted in essence by the cylindrical part 37 of the screw 3, slides in the bore 25, efficiently guiding the screw 3 with respect to the component 2, this avoiding misalignment of the axes $X_1$, $X_2$ and $X_3$ and thus guaranteeing a correct relative positioning of the truncated bearing surfaces 12 and 24.

According to another approach, the element E may be assembled, from the configuration of FIG. 2, by impacting the principal component 1 in the direction of the principal component 2 so that the cylindrical part 37 of the screw 3 is in essence driven in the housing 25. Impaction takes place until the components 1 and 2 come into contact. It is then possible to unscrew the screw 3 with respect to the component 1 and to screw it in the tapping 26, which enables an effort of relative immobilization of components 1 and 2 to be exerted on the surface 422, and thanks to the flange 34.

Figure 6:
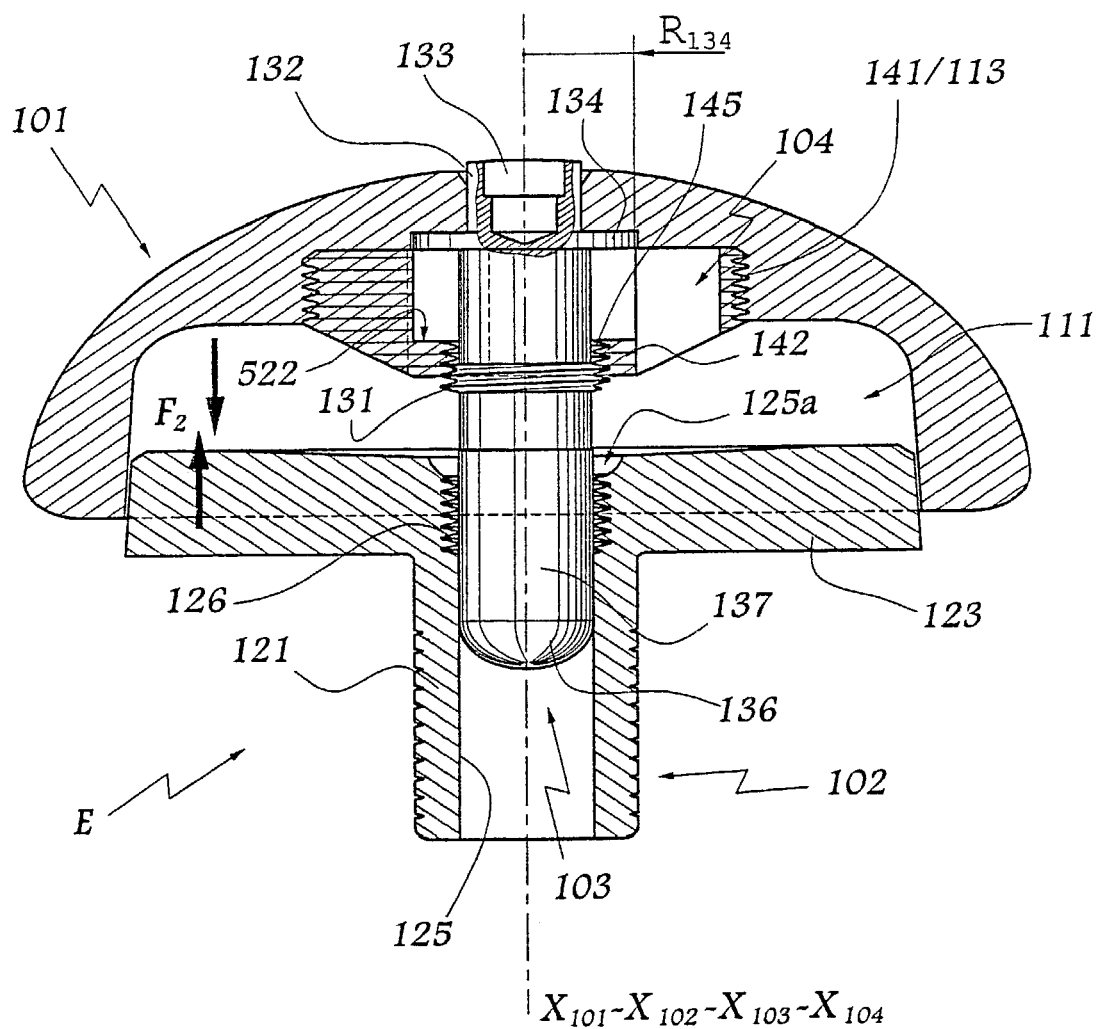
FIG. 6 is a view similar to FIG. 3 for a prosthetic element in accordance with a second form of embodiment of the invention.
Figure 7:
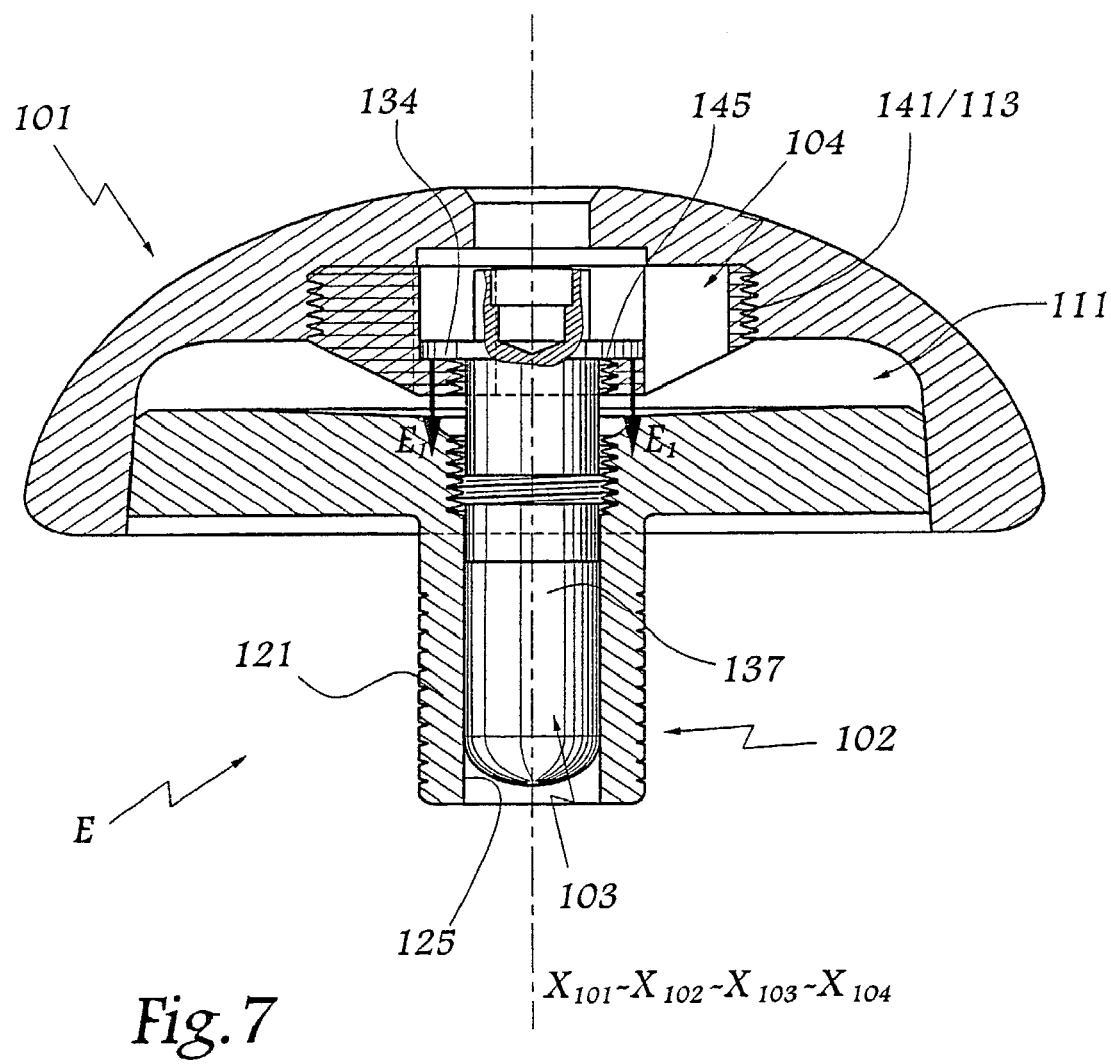
FIG. 7 is a view similar to FIG. 5 for the element of FIG. 6.

In the second form of embodiment of the invention, shown in FIGS. 6 and 7, elements similar to those of the first embodiment bear identical references increased by 100. The prosthetic element E of this embodiment comprises two principal components 101 and 102 as well as a screw 103 and a bush 104. The component 102 is provided to be engaged in a central recess 111 of the component 101. $X_{101}$, $X_{102}$, $X_{103}$ and $X_{104}$ respectively denote the central axes of the elements 101 to 104. These axes merge in the positions of FIGS. 6 and 7. The bush 104 is provided with a thread 141 allowing it to be screwed in a tapping 113 provided in the component 101. The bush 104 is also provided with a central tapping 145 provided to cooperate with a thread 131 made on the screw 103.

As previously, the screw 103 is provided, at its upper end 132, with a housing 133 for a wrench. A flange 134 of relatively great radius $R_{134}$ is also provided on the screw 103, this flange being able to come into abutment against a lateral surface 522 of a ring 142 formed by the bush 104.

A bore 125 is made in the anchoring shank 121 of the component 102 and passes through a plate 123 intended to be engaged in a central recess 111 of the component 101.

The bore 125 is provided, in the vicinity of its inlet zone 125a, with a tapping 126 oriented and configured in order to be able to cooperate with the thread 131 of the screw 103.

A cylindrical part 137 and an end 136 of the screw 103 constitute a finger for guiding and centering this screw in the housing 125.

Functioning is as follows:

In order to assemble the element E, the screw 103 is introduced in the bush 104, causing end 136 to traverse a central recess of the bush 104, this recess being bordered by the tapping 145. The screw 103 is then screwed in the tapping 145 and the sub-assembly 103–104 thus produced is screwed on the component 101 thanks to the thread 141 and the tapping 113. It is then possible to pre-center the component 101 with respect to the component 102, possibly already in place on a patient, by the cooperation of the finger 136–137 and the housing 125, then to approach these elements towards each other as represented by arrows $F_2$ in FIG. 6.

It is then possible to unscrew the screw 103 with respect to the bush 104 while pushing it in the direction of the plate 123, the translation of the screw 103 with respect to the component 102 being guided by the finger 136–137. The components 101 and 102 may then be approached towards each other, as shown in FIG. 6, and the screw 103 screwed in the tapping 126 thanks to the thread 131, which makes it possible to obtain a firm immobilization of the elements 102 and 103 with respect to each other, thanks to an effort $E_1$ exerted by the flange 134 on the surface 522.

As mentioned with reference to the first form of embodiment, another process of assembly may consist, from the position of FIG. 6, in impacting the component 101 in the direction of the component 102 so as to bring these components into contact. The screw 103 is then unscrewed with respect to the bush 4 then screwed in the tapping 126 in order to maintain these components in contact with each other, thanks to the effort $E_1$.

The thread 131 of the second form of embodiment performs the functions of the threads 31 and 35 of the first embodiment.

The invention has been represented with a prosthetic component intended to equip the glenoid cavity of a shoulder. However, it is applicable to any type of prosthetic element comprising two principal components.

What is claimed is:

1. A prosthetic element comprising first and second principal components, said first principal component including an outer articular surface (S), a threaded tapping within each of said first and second principal components, a screw for securing said first and second principal components together, said screw being provided with means including at least one threaded section for successively engaging said threaded tappings within said first and second components, said screw including at least one radial element which abuts against a stop within said first principal component and further including a non-threaded portion which extends from an end of said screw and towards said at least one threaded section thereof and which non threaded portion forms a guide and centering finger which is slidable in a bore in said second principal component so as to align said screw with said threaded tapping of said second principal component.

2. The prosthetic element of claim 1, wherein said at least one radial element is formed by a radial flange made between first and second threaded sections on said screw.

3. The prosthetic element of claim 1, wherein said stop is annular and surrounds said screw.

4. The prosthetic element of claim 3, wherein said stop is formed by a face of a bush screwed into another threaded tapping of said first principal component and said threaded tapping engageable by said at least one threaded section of said screw being formed in said bush.

5. The prosthetic element of claim 1, wherein said first principal component is provided with a recess defined by an annular side wall bearing surface, and said second principal component includes a plate having an outer annular wall defining a bearing surface for cooperatively engaging said side wall bearing surface of said recess as said at least one threaded section of said screw engages within said threaded tapping of said second component.

6. The prosthetic element of claim 5, wherein said bearing surfaces are respectively centered on a central axis of said screw and on a central axis of said bore.

7. The prosthetic element of claim 1, wherein said threaded tapping of said second component is formed in said bore.

8. The prosthetic element of claim 1, wherein said outer articular surface of said first principal component is convex and includes an internal recess in which said screw may be mounted and said second principal component at least partially engaged.

9. The prosthetic element of claim 1, wherein said bore for receiving said guide and centering finger is made in a shank for anchoring said second principal component in a bone.

10. A prosthetic element comprising first and second principal components, a threaded tapping within each of said first and second principal components, a screw for securing said first and second principal components together, said screw including at least one radial element which abuts against a stop within said first principal component and further including a non-threaded end portion forming a guide adapted to slide in a bore in said second principal component so as to align said screw within said bore and said screw being provided with first and second threaded sections which are spaced relative to one another so as to engage in a successive manner with said threaded tappings within said first and second principal components so that said first threaded section initially engages said threaded tapping within said first principal component after which said second threaded section engages said threaded tapping within said second principal component.

11. A prosthetic element comprising first and second principal components, a threaded tapping within each of said first and second principal components, a screw for securing said first and second principal components together, said screw including at least one radial element which abuts against a stop within said first principal component and further including a non-threaded end portion forming a guide adapted to slide in a bore in said second component so as to align said screw within said bore and said screw being provided with a threaded section adapted to engage, in a successive manner, with said threaded tappings within said first and second principal components.

12. Process for assembling a prosthetic element comprising two principal components and a screw, comprising the steps of:
   immobilizing said screw with respect to a first principal component by screwing said screw in a first threaded tapping within said first principal component;
   sliding a bore of said second principal component over a free end of said screw which projects from said first principal component;
   pushing said first and second principal components towards each other, causing said end of said screw to slide in said bore;
   unscrewing said screw with respect to said first threaded tapping, and thereafter
screwing said screw in a second threaded tapping made in said second principal component to thereby secure said first and second principal components together.

13. Process for assembling of a prosthetic element comprising two principal components and a screw, comprising the steps of:
   immobilizing said screw with respect to a first principal component by screwing said screw in a first threaded tapping within said first principal component;
   placing a bore of said second principal component over a free end of said screw which projects from said first principal component;
   impacting one of said first and second principal components in a direction of the other so as to bring them closer, causing said free end to slide in said bore until said components are brought into contact with each other;
   unscrewing said screw with respect to said first threaded tapping; and thereafter screwing said screw in a second tapping made in said second principal component to secure said first and second principal components in contact with one another.

14. A prosthetic element for forming a part of a prosthesis, the prosthetic element comprising; a first component having an outer articular suface (S), a central recess, and first and second threaded tappings therein, a second component including a plate adapted to be at least partially cooperatively seated within said central recess and an anchoring shank having an internal bore, said second component having a threaded tapping therein aligned with said bore, a screw including at least one threaded section and an outwardly extending flange, said screw having a first non threaded end portion of a size to be guidingly received within said bore, a threaded annular bush selectively engageable with said first threaded tapping of said first component and serving as a stop to engage said flange of said screw to secure said screw within said first component, and said at least one threaded section of said screw being successively engageable with said second threaded tapping within said first component and said threaded tapping within said second component.

15. The prosthetic element of claim 14 wherein an opening is provided through said outer articular surface (S) into said central recess through which a tool may be selectively inserted, and said screw having a second end portion configured to be cooperatively engaged by the tool.

16. The prosthetic element of claim 15 wherein said second threaded tapping is formed within said opening to cooperatively receive said at least one threaded section of said screw.

17. The prosthetic element of claim 14 wherein said screw includes first and second threaded sections that are separated by said flange, and said second threaded tapping within said first component and said threaded tapping within second component have threads extending in opposite directions.

18. A prosthetic element for forming a part of a prosthesis, the prosthetic element comprising; a first component having an outer articular suface (S), a central recess, and a first threaded tapping, a second component including a plate adapted to be at least partially cooperatively seated within said central recess and an anchoring shank having an internal bore, said second component having a threaded tapping aligned with said bore, a screw including at least one threaded section and an outwardly extending flange, said screw having a first non threaded end portion of a size to be guidingly received within said bore, said threaded tapping of said second component being threadingly engageable with said at least one threaded section of said screw, a threaded annular bush selectively engageable with said first threaded tapping of said first component and serving as a stop to engage said flange of said screw to secure said screw within said first component, and said threaded annular bush including a threaded tapping which is axially aligned with said threaded tapping of said second component and said at least one threaded section of said screw being successively threadingly engageable with said threaded tapping of said threaded annular bush that is secured within said first component and said threaded tapping within said second component.

19. The prosthetic element of claim 18 wherein said screw includes a single threaded section extending between said flange and said non threaded end portion.

20. The prosthetic element of claim 18 wherein an opening is provided through said outer articular surface (S) into said central recess through which a tool may be selectively inserted, and said screw having a second end portion configured to be cooperatively engaged by the tool.

* * * * *